United States Patent [19]

Caprio, Jr.

[11] 4,187,844
[45] Feb. 12, 1980

[54] ANKLE SUPPORTER

[76] Inventor: Louis W. Caprio, Jr., 132 Eustis St., Revere, Mass. 02115

[21] Appl. No.: 959,998

[22] Filed: Nov. 13, 1978

[51] Int. Cl.² ............................................. A61F 13/06
[52] U.S. Cl. ................................................... 128/166
[58] Field of Search .................. 128/166, 166.5, 80 H

[56] References Cited

U.S. PATENT DOCUMENTS

| | | | |
|---|---|---|---|
| 851,950 | 4/1907 | Le Mat | 128/166 |
| 893,064 | 7/1908 | Ferris | 128/166 |
| 938,440 | 10/1909 | Sescila | 128/166 |
| 1,084,197 | 1/1914 | Collis | 128/166 |
| 1,090,906 | 3/1914 | Collis | 128/166 |
| 2,994,322 | 8/1961 | Cullen et al. | 128/80 H |

FOREIGN PATENT DOCUMENTS 31283  1/1908  Fed. Rep. of Germany ........... 128/166

*Primary Examiner*—Lawrence W. Trapp
*Attorney, Agent, or Firm*—Milton Oliver

[57] ABSTRACT

A lace-on pliable sleeve for the prevention of sprained ankles during athletic activities. A separate tongue portion is secured in place on the foot beneath the eyelets of the sleeve by passing one or more laces through holes in the tongue. The configuration of the sleeve itself resembles that of a sock cut away at the toe and the heel. The inner layer of the sleeve comprises a Y-shaped piece of pliable material, the arms of the Y being sewn together to form a seam disposed along the sole of the wearer's foot. This inner layer is reinforced and stiffened by a plurality of strips of material sewn to the outer surface thereof along the lacing edges, around the lower periphery and along and across the sides thereof. The stiffening strips reinforce the ligaments of the ankle and the metatarsal bones of the foot.

4 Claims, 5 Drawing Figures

ANKLE SUPPORTER

BACKGOUND OF THE INVENTION

The present invention relates generally to lace-on flexible braces for the ankle, and more particularly to flexible braces having stiffening elements paralleling the natural ligaments of the ankle and bones of the foot.

The shift away from high-topped athletic shoes or sneakers to low-cut sneakers has increased the probability of sprained ankles during athletic activity such as tackling in football or jumping for rebounds in basketball. Two of the solutions attempted to relieve this problem have been to use elastic bandages wrapped around the ankle or to tape the ankle in such a manner as to prevent rotation of the foot in a direction which would strain the ligaments, particularly if they are in a weakened condition. The elastic bandage has the disadvantage of tending to loosen quite frequently, forcing the wearer to choose between interrupting his or her participation in a game and continuing to play without support. The application of adhesive tape by trainers or coaches, on the other hand, is expensive both in terms of staff time and in terms of the quantity of tape applied and discarded by a team each day. Furthermore, tape tends to loosen under the influence of perspiration, is uncomfortable to remove, and leaves a sticky residue.

To avoid these difficulties, a number of reusable ankle supporters have been devised, including those disclosed in U.S. Pat. Nos. 3,028,861, 3,073,305, 3,618,598 and 3,970,083. Such devices, while providing some support for the ankle, do not afford the degree of support for the metatarsal bones of the foot provided by the present invention. The five metatarsal bones of each foot connect the toe bones with the bones of the ankle and form the arch of the foot. The metatarsal bone connected to the little toe is the one closest to the ground and bears much of the initial impact when the foot lands on the ground after a jump or similar athletic activity, particularly when the foot lands at an angle, with its outer edge along the floor. Certain prior art devices, while providing reinforcing strips vertically on either side of the ankle and crosswise over the bumps on the ankle known as the medial (inner) malleolus and the lateral (outer) malleolus, have no reinforcing strips running from the ankle in the direction of the toes to support the metatarsals.

Accordingly, it is an object of the present invention to provide a lace-on sleeve supporting both the ankle ligaments and the metatarsal bones.

It is another object of this invention to provide an ankle supporter which will not come loose during activity, yet which may be fastened about the ankle by the wearer without the assistance of a coach or trainer.

It is yet another object of the present invention to provide an ankle supporter which is sufficiently flexible to be worn comfortably over an injured ankle, yet sufficiently reinforced to prevent further injury to the ankle.

FEATURES OF THE INVENTION

To accomplish these and other objects, the ankle supporter of this invention has among its many features a flexible single-piece fabric sleeve, a row of lacing eylets along each of two facing edges, and reinforcing strips sewn on the outside of the sleeve around the peripheral edge nearest the toes, along each side of the sleeve from the lower periphery to the upper edge and from the lacing edge to the edge nearest the heel.

A separate tongue, preferably comprising a layer of fabric sewn to a layer of polyethylene, is secured in place on the foot beneath the eyelets of the sleeve by passing one or more laces through holes in the tongue.

BRIEF FIGURE DESCRIPTION

Other objects, features and advantages will appear from the following description of a preferred embodiment of the invention, as shown on the attached drawings, in which.

DETAILED DESCRIPTION OF THE DRAWINGS

Figure 1:
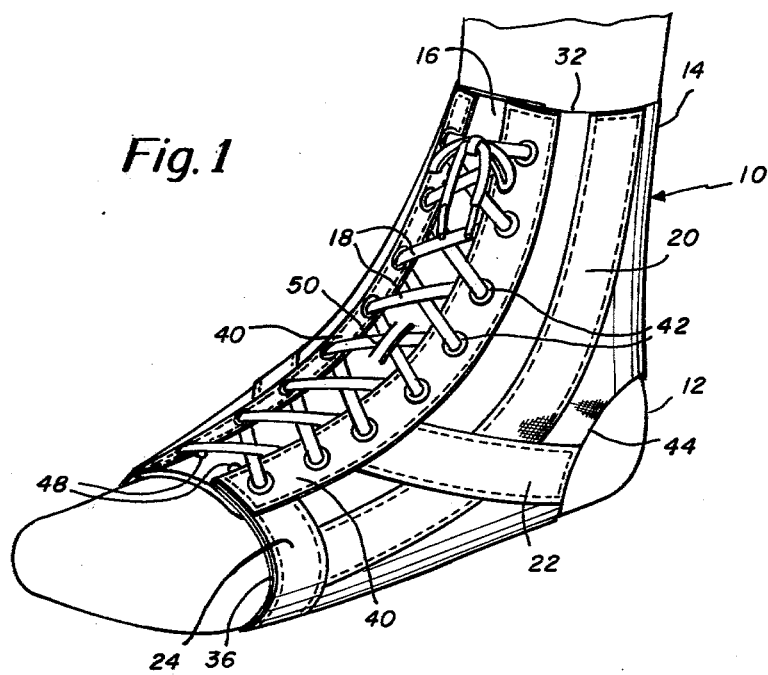
FIG. 1 is a perspective view of the ankle supporter laced onto a person's left foot.

There is shown in FIG. 1 an ankle supporter 10 laced onto a left foot 12. The ankle supporter comprises a flexible sleeve 14 secured across tongue 16 by conventional laces 18. Sleeve 14 is reinforced by lower peripheral strip 24 and on each side of the foot 12 by a longitudinal stiffening strip 20 and a transverse stiffening strip 22.

Figure 2:
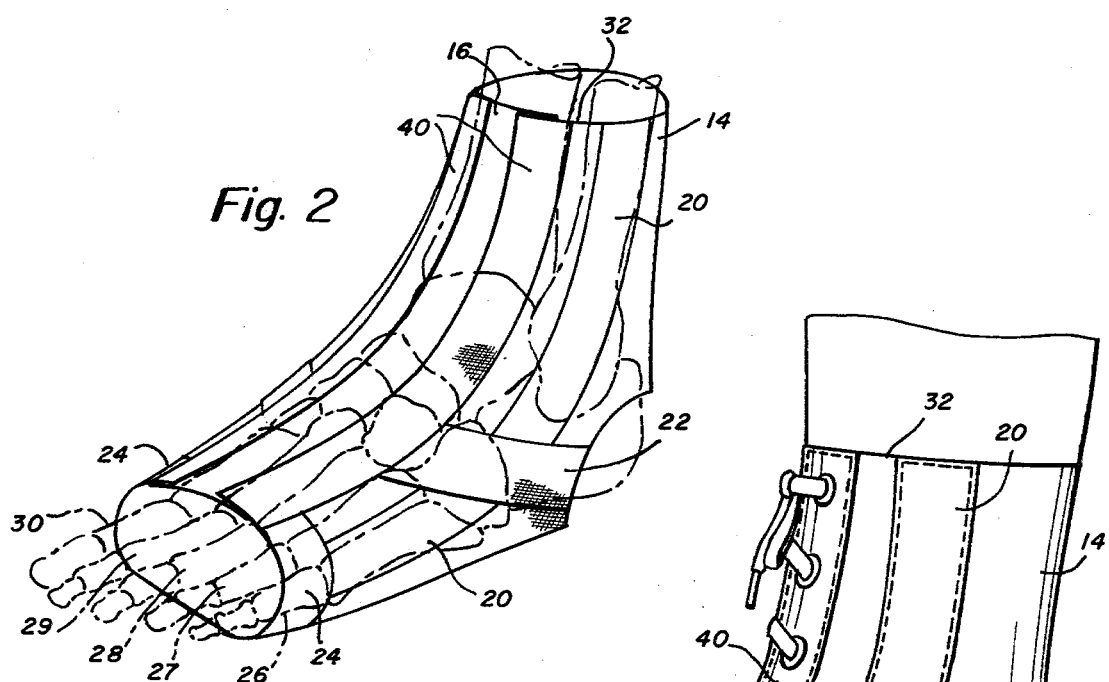
FIG. 2 is a simplified schematic view of the supporter from the same perspective as FIG. 1 and showing the location of the metatarsal bones.

As shown more clearly in FIG. 2, the reinforcing strip 20 on the lateral (outer) side of the foot curves below the ankle to overlie and protect metatarsal bone 26 connected to the little toe. Also illustrated are metatarsal bones 27, 28 and 29 connected to the middle toes and metatarsal bone 30 connected to the big toe.

Figure 3:
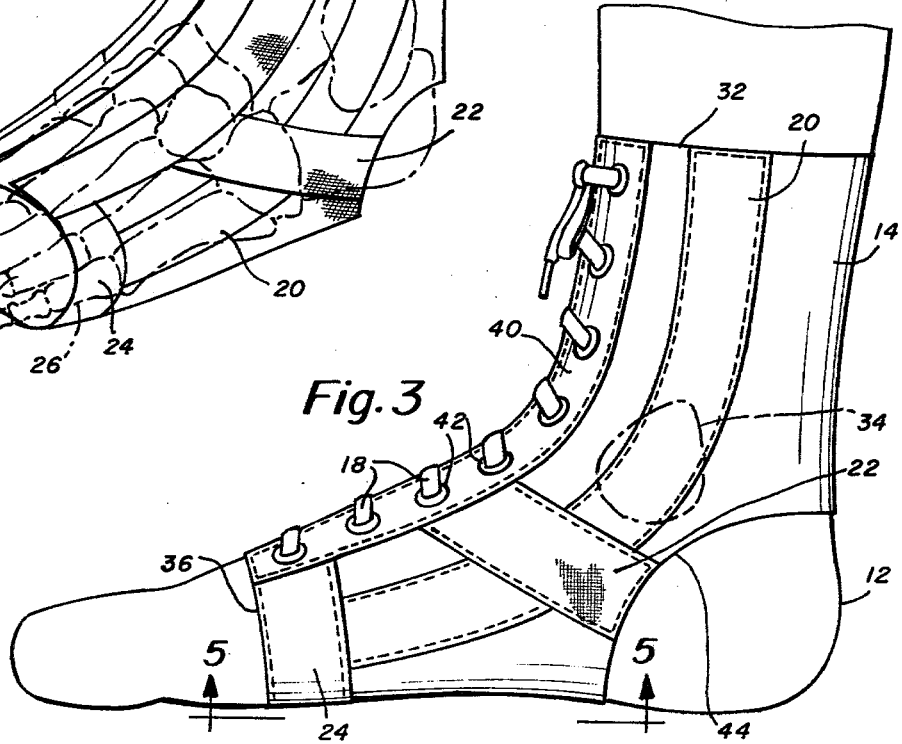
FIG. 3 is a side elevational view of the supporter showing the relationship of the reinforcing strips to the lateral malleolus of the foot.

FIG. 3 is a side elevational view of the ankle supporter of this invention. Although the supporter is bilaterally symmetrical and may be worn on either foot, the view shown illustrates the contour of the lateral (outer) side of a wearer's left foot. THe longitudinal reinforcing strip 20 is stitched at its upper end to the upper edge 32 of the supporter, then extends vertically down over the protruding knob of bone known as the lateral malleolus and curves toward the toe end of the supporter, where its end is stitched under the lower peripheral reinforcing strip 24.

Along the facing edges 38 of sleeve 14 adjacent to tongue 16 are stitched lacing strips 40 which are pierced by and help support a plurality of lacing eyelets 42. These eyelets 42 are of conventional steel construction and are preferably evenly spaced and eight in number along each of the lacing strips 40. Fastened to, and preferably beneath, each of the lacing strips 40 is one end of a transverse reinforcing strip 22, which extends across longitudinal reinforcing strip 20 and terminates at the concave cutaway edge 44 of the supporter adjacent the heel of the foot 12. Unlike certain prior art transverse reinforcing strips, the strip 22 passes below rather than across the lateral malleolus 34.

Figure 4:
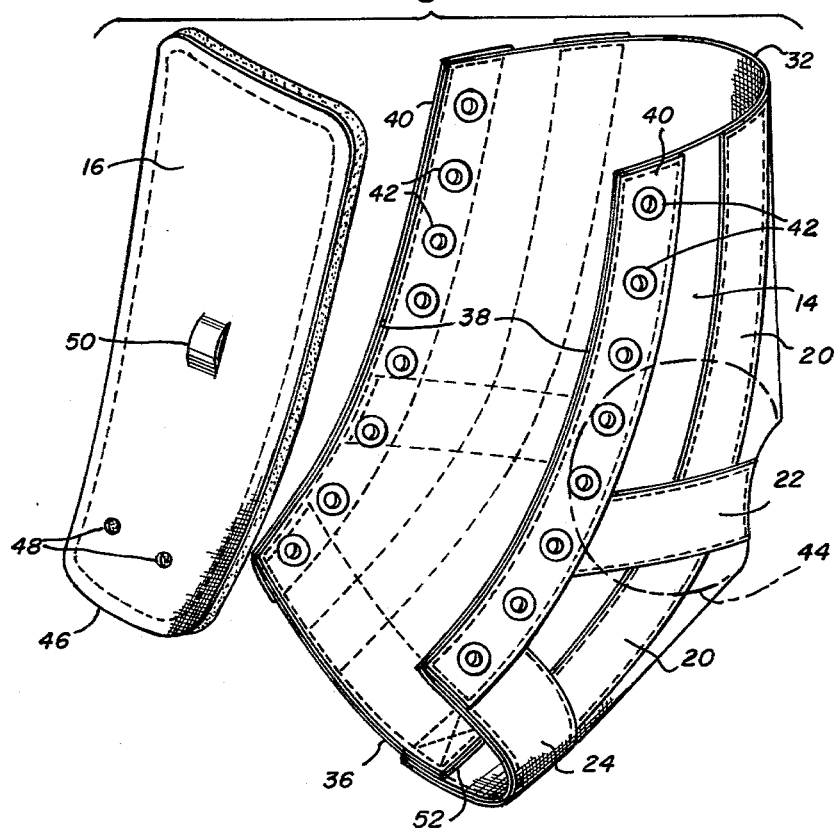
FIG. 4 is an enlarged and exploded perspective view of the supporter showing the details of its construction.

FIG. 4 is an enlarged and exploded perspective view of the ankle supporter 10, with the laces 18 removed for clarity. Tongue 16 is basically trapezoidal, being slightly narrower at its toe end, and comprises a sheet of fabric stitched around its periphery to a flat piece of polyethylene. This enables it to mold to the wearer's foot after one use. Near and parallel to its toe end 46 are two spaced holes 48 through which the lace between the lowermost of the eyelets 42 on each of the lacing strips 40 may be passed to secure the tongue under the facing edges 38 of the sleeve 14.

The ends of the lace 18 are threaded through the next three eyelets on each of the lacing strips 40 in the conventional criss-cross fashion, while the tongue 16 is held longitudinally against the foot. Two parallel spaced slits 50, preferably about two centimeters in length, penetrate the fabric and polyethylene layers of the tongue 16 in a direction parallel to facing edges 38 of the sleeve 14. The ends of lace 18 pass into one slit underneath the tongue, and out the other slit between the fourth and fifth pair of eyelets 42, thereby stabilizing the tongue 16 against sidewise rotation. The laces 18 are tied at the top like conventional shoelaces. Those skilled in the art will appreciate that this arrangement allows one size of sleeve to fit a wide range of sizes of feet. It also allows an athlete to support his or her ankles under more consistent pressure from day-to-day than is usually achieved with taping by a trainer. However, the foregoing description is not intended to restrict the scope of my invention, since alternative fasteners, such as zippers, may also be used.

The sleeve 14 is preferably composed of a Y-shaped piece of triple-laminated, nylon-reinforced Facilon vinyl. The "tail" of the Y comprises the section of the sleeve 14 adjacent the Achilles tendon, while the "arms" of Y are sewn together along bottom seam 52 to form the section of the sleeve 14 adapted to encircle the arch of the foot 12, and the inside edges of the "arms" form the concave cutaway edge 44 adjacent the heel.

Other pieces of the same vinyl fabric may be used as reinforcing strips of the sleeve 14. These strips are preferably attached to the outer surface of the sleeve 14 by a row of machine-sewn stitches adjacent each edge of each strip. The first strip is a longitudinal strip 20 sewn on each side of the foot 12, curving from the upper edge 32 of the supporter over the malleolus 34 to its lower edge 36 and having roughly the configuration of a boomerang. The upper section of this strip 20 parallels and supports the ligaments of the ankle, while the lower section parallels and supports the metarsal 26 connected to the little toe. Across one end of each of the strips 20 is stitched a lower peripheral reinforcing strip 24 which connects the facing edges 38 of the sleeve 14 and passes over bottom seam 52. This strip 24 and the lace 18 together support the arch by binding the metatarsals 26-30 together. Another strip which is stitched across each strip 20 is transverse reinforcing strip 22, which runs from facing edge 38 to cutaway heel edge 44, passing between the malleolus 34 and the lower edge 36.

Across one end of transverse strip 22 and of lower peripheral strip 24 and along each facing edge 38 is stitched a lacing reinforcing strip 40. Each strip 40 is pierced by a row of conventional lacing eyelets 42, preferably eight in number. The eyelets 42 each fasten the sleeve 14 and the strip 40 tightly together, as well as preventing tearing of the fabric under the tension of the laces 18.

Figure 5:
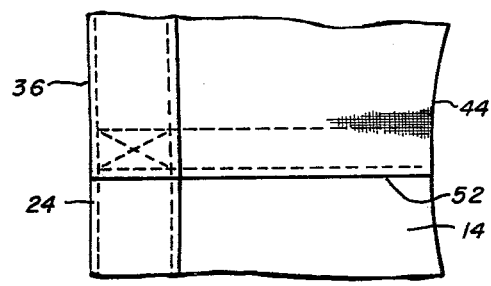
FIG. 5 is a fragmentary view of the bottom seam taken along line 5—5 of FIG. 3.

As shown in FIG. 5, seam 52 is created by lapping the fabric of the sleeve 14 and joining the lapped edges by two parallel rows of stitching. An additional criss-cross of stitching reinforces the portion of the seam 52 adjacent lower sleeve edge 36 crossed by lower peripheral reinforcing strip 24. The location of the seam beneath the sole of the foot 12 minimizes friction and promotes wearing comfort.

The supporter 10 as described above provides greater plantar and dorsal flexion than taping while providing the same protection against sprains. It also permits greater eversion and inversion of the foot than tape, which is necessary for lateral defensive moves in basketball or sliding to a base in baseball.

Another benefit of allowing slight longitudinal roll of the foot (inversion and eversion) is that it reduces stress on the knee joint. Normally, when an athlete's leg strikes the ground, some of the resulting vertical deceleration is translated into rotation of the foot toward its inner or outer edge, cushioning the impact felt by the knee joint. Taping the foot stiff removes this cushion and can lead to knee joint problems. The present invention, while preventing rotation from proceeding so far as to allow injury, leaves some rotation and some cushioning effect, protecting the knee joint.

While I have described a preferred embodiment of my invention, those skilled in the art will recognize that many variations could be made therein without departing from its spirit. Therefore, I do not intend to limit the scope of my invention to the single embodiment shown and described. Rather, I intend to be limited only by the scope of the appended claims.

What I claim is:

1. An ankle supporter adapted to be fastened about a foot and ankle, comprising:
    a flexible fabric sleeve having a lower peripheral edge and two facing edges,
    means for fastening said facing edges together,
    a longitudinal reinforcing strip stitched to a side of said sleeve, passing over the lateral malleolus of the foot and extending below the ankle to parallel the metatarsal bones of the foot, and
    a transverse reinforcing strip intersecting said longitudinal reinforcing strip between the lateral malleolus and said lower peripheral edge.

2. An ankle supporter as set forth in claim 1, wherein said means for fastening comprises a row of eyelets along each of said facing edges, a lace through said eyelets, and a tongue laced between said eyelets and said foot.

3. An ankle supporter as set forth in claim 2, wherein said tongue comprises a sheet of fabric stitched to a sheet of polyethylene.

4. An ankle supporter as set forth in claim 1, wherein each of two sides of said sleeve is reinforced by a longitudinal strip and a transverse strip.

* * * * *